United States Patent
Hunziker et al.

(10) Patent No.: US 10,281,442 B2
(45) Date of Patent: May 7, 2019

(54) SENSOR DEVICE

(71) Applicant: Sensirion AG, Stafa (CH)

(72) Inventors: Werner Hunziker, Stafa (CH); Stephan Braun, Stafa (CH)

(73) Assignee: Sensirion AG, Stafa (CH)

( * ) Notice: Subject to any disclaimer, the term of this patent is extended or adjusted under 35 U.S.C. 154(b) by 438 days.

(21) Appl. No.: 14/526,898

(22) Filed: Oct. 29, 2014

(65) Prior Publication Data
US 2015/0143874 A1 May 28, 2015

(30) Foreign Application Priority Data
Nov. 6, 2013 (EP) .................................. 13005237

(51) Int. Cl.
*B81B 7/00* (2006.01)
*B81C 1/00* (2006.01)
*G01N 33/00* (2006.01)

(52) U.S. Cl.
CPC ....... *G01N 33/0009* (2013.01); *B81B 7/0029* (2013.01); *B81C 1/00896* (2013.01); *G01N 2033/0095* (2013.01); *Y10T 156/1052* (2015.01)

(58) Field of Classification Search
CPC .... H04R 1/28; H04R 2460/11; H04R 25/456; H04R 2201/003; G01L 19/0084; G01L 19/141; B01D 53/228; B01D 69/12; B01D 71/06; B23B 3/00; B32B 37/18; B32B 38/0004; B32B 3/266; B32B 3/0235; B81B 2201/0235; B81B 2201/0242; B81B 2201/0257; B81B 2201/0264; B81B 7/0041; B81B 7/0058; B81B 7/0061; B81B 7/0029; B81C 1/00293; B81C 2201/053; B81C 1/00896; G01N 33/0009; G01N 2033/0095; Y10T 156/1052

See application file for complete search history.

(56) References Cited

U.S. PATENT DOCUMENTS

| 3,999,122 | A | 12/1976 | Winstel et al. |
| 6,528,875 | B1 | 3/2003 | Glenn et al. |
| 6,700,174 | B1 * | 3/2004 | Miu ................ G01L 9/0051 257/419 |
| 8,902,604 | B2 * | 12/2014 | Zoellin ............ H04R 19/005 361/761 |

(Continued)

FOREIGN PATENT DOCUMENTS

| DE | 102005043690 | 3/2007 |
| EP | 2053651 | 4/2009 |

(Continued)

OTHER PUBLICATIONS

Pall Corporation, "Material Selection for Venting Applications", 2007, pp. 1-10.

*Primary Examiner* — Randy W Gibson
*Assistant Examiner* — Gedeon M Kidanu
(74) *Attorney, Agent, or Firm* — Cooper & Dunham LLP

(57) ABSTRACT

A sensor device comprises a sensitive element (1) and a support (2) for the sensitive element, the support having a surface (3) with an access opening (4) to the sensitive element (1). A layer of adhesive material (5) covers at least parts of the surface (3). A venting medium (6) extends over the entire surface (3) of the support (2) and the access opening (4) and is attached to the support (2) by the layer of adhesive material (5).

11 Claims, 4 Drawing Sheets

(56) References Cited

U.S. PATENT DOCUMENTS

| | | | |
|---|---|---|---|
| 2005/0104204 A1 | 5/2005 | Kawakubo et al. | |
| 2006/0179942 A1 | 8/2006 | Fukaura et al. | |
| 2006/0270108 A1 | 11/2006 | Farnworth et al. | |
| 2008/0048822 A1 | 2/2008 | Ehrhom | |
| 2008/0283991 A1 | 11/2008 | Reinert | |
| 2008/0315230 A1 | 12/2008 | Murayama | |
| 2009/0212397 A1 | 8/2009 | Tuttle | |
| 2010/0212433 A1* | 8/2010 | Hunziker | G01D 11/245 73/706 |
| 2010/0225000 A1 | 9/2010 | Sugizaki et al. | |
| 2011/0018076 A1* | 1/2011 | Pahl | B81B 7/0061 257/415 |
| 2012/0212925 A1* | 8/2012 | Zoellin | H04R 19/005 361/807 |
| 2013/0094684 A1* | 4/2013 | Ehrenpfordt | B81C 1/0023 381/332 |
| 2013/0126992 A1 | 5/2013 | Ehrenpfordt et al. | |
| 2013/0157163 A1 | 6/2013 | Nanba et al. | |
| 2013/0263996 A1* | 10/2013 | Holliday | B81B 7/0058 156/69 |
| 2014/0028340 A1* | 1/2014 | Graf | B81C 1/00333 324/756.01 |

FOREIGN PATENT DOCUMENTS

| | | |
|---|---|---|
| EP | 2154713 | 2/2010 |
| EP | 2273261 | 1/2011 |
| EP | 2481703 | 8/2012 |
| EP | 2482310 | 8/2012 |
| WO | 0156920 | 8/2001 |
| WO | 2005102911 | 11/2005 |
| WO | 2013138286 | 9/2013 |

* cited by examiner

SENSOR DEVICE

CROSS REFERENCE TO RELATED APPLICATIONS

This application claims the priority of European patent application 13005237.6, filed on Nov. 6, 2013, the disclosure of which is incorporated herein by reference in its entirety.

FIELD OF THE INVENTION

The present invention relates to a sensor device and a method for manufacturing a sensor device.

BACKGROUND OF THE INVENTION

Sensor devices and methods for manufacturing sensors devices are known. In the European patent application no. EP 2 481 703 A1 for example, there is described a method for manufacturing a sensor device, wherein a spacer is arranged at the front side of a substrate at which front side a sensitive element is arranged, too. Holes are etched for building vias extending through the substrate between the front side of the substrate and its back side. After etching, the holes are filled with conductive material to complete the vias. The spacer provides protection to the sensitive element and the sensor device throughout the manufacturing process.

In sensor devices the sensitive element may be sensitive to contaminants, such as particles and/or liquids, e.g. water or oil. When a sensor device is manufactured, especially in a batch process, there may be contaminations arising during device singulation, e.g. by sawing or laser cutting.

SUMMARY OF THE INVENTION

Hence, according to a first aspect of the invention, there is provided a sensor device, with a sensitive element and a support for the sensitive element. The sensitive element is protected against contaminants, such as particles, and/or liquids, such as water or oil, by means of a venting medium.

The term "venting medium" as used herein designates a medium that enables the passage of gas through the venting medium while liquids and contaminants are in essence repelled at the surface. The venting medium may be a venting layer or a venting film.

In a preferred embodiment the venting medium is based on or made from one or more of polymer—especially fluoropolymer, PTFE, acrylic copolymer, polyethersulfone polymer—glass fiber, porous organic material or porous inorganic material.

As different types of venting media may differ in their ability to repel different kinds of liquids, e.g. water or oil based liquids, a combination of several venting media in form of a material mixture or in form of a multi-layer may be used as a venting medium.

Additionally, the venting medium may protect the sensing element to some extent against direct mechanical contact from outside of the sensor device. The term "support" as used herein may contain one or more of a die, a chip, a substrate, e.g. a glass substrate or a ceramic substrate or a semiconductor substrate, and in particular a silicon substrate, as well as means of contacting, e.g. one or more of wire bonds, through-silicon-vias, a ball grid array, a land grid array, T-contacts, a lead frame or a printed circuit board, and packaging, e.g. a mold or a silicon cap or a silicon interposer. Furthermore, it may contain additional features to support the operation of the sensitive element, e.g. a heater structure to heat the sensitive element or a suspended membrane to achieve thermal insulation, or features to process the measurement signal of the sensitive element, e.g. an integrated processing circuit.

The term the "surface of the support" as used herein refers only to the surface of the support which contains the access opening to the sensitive element. For example, if the support has a rectangular footprint and if the support has one access opening in what is named to be the front-side of the support, the surface of the front-side that contains the access opening is referred to as the surface of the support. If a support contains an access opening in what is named to be the backside, this surface is referred to as the surface of the support.

In another embodiment the support may have access openings on several sides, for example on the front- and back-side. The different surfaces with access openings, e.g. front- and back-side, may be covered with each an individual venting medium, each attached to the relevant individual surface.

The venting medium is attached to the support for the sensitive element by means of a layer of adhesive material. The attachment is done in such a way that the venting medium covers the access opening in the support to the sensitive element, which may be relevant pathways for contamination of the sensitive element. This may be achieved by covering at least parts of the surface that gives way to the access opening to the sensitive element with a layer of adhesive material and attaching the venting medium by this means. The adhesive material may for example contain polymers or filled polymers.

Where the venting medium is in contact with adhesive material, the adhesive material may impact the passage of gas through the venting medium. The adhesive material may for example block pores of the venting medium if any. This may however not affect the functionality of the present invention, as in the areas where the venting medium extends over the sensitive element there is no layer of adhesive material present and therefore the passage of gas to the sensitive element may not be affected significantly.

In a preferred embodiment, the sensitive element may be sensitive to one or more of pressure, gas, humidity, gas flow and differential pressure. Hence, in a preferred embodiment, the sensor device may represent one or more of a pressure sensor, a microphone, a humidity sensor, or a gas flow sensor.

In one embodiment, the support comprises a substrate such as a semiconductor substrate and optionally comprises a carrier for the substrate, such as a lead frame or a printed circuit board. In an embodiment, the support further comprises a spacer material which spacer material is applied between the substrate or, if applicable, the carrier and the layer of adhesive material. The spacer material may serve to increase the separation between the sensitive element and the venting medium. The spacer material can either be dedicated material or a thicker layer of adhesive material, of about more than 100 um thickness, which can serve the purpose of the spacer material at the same time. In a preferred embodiment, the spacer is based on or made from one or more of polymer, filled polymer, mold compound, silicon or glass.

The sensitive element may in one embodiment be located in a cavity in the support, wherein the cavity opens out into the surface and thereby defines the access opening.

In a preferred embodiment, a top element is added on a part of the venting medium. This top element may serve as protection for the venting medium, to apply a label, an identification mark and/or an alignment mark. In a preferred embodiment the top element is based on or made from one or more of polymer, filled polymer, mold compound, silicon, glass or metal.

According to another aspect of the present invention, a method is provided for manufacturing a sensor device. A sensor support assembly is provided which contains an array of sensitive elements for manufacturing a plurality of sensor devices, and preferably contains a two dimensional array of sensitive elements. The sensor support assembly has a surface with access openings to the sensitive elements. Analogously to the description above for the sensor device, the surface refers to the surface which contains the access openings.

In the following, a layer of adhesive material is deposited on at least parts of the surface of the sensor support assembly. The layer of adhesive material may be deposited on at least parts of the surface of the sensor support assembly by printing, dispensing, stamping, spin coating and/or lamination. It may be structured directly during the deposition process or after deposition, e.g. by a photo-lithography based process. In one embodiment, spacer material is deposited on the surface of a substrate or another carrier contributing to the support prior to deposition of the layer of adhesive material and then the layer of adhesive material is deposited on at least parts of the spacer material.

In the following, a venting medium is arranged over the entire surface of the sensor support assembly and the access openings. The venting medium is attached to the sensor support assembly by the layer of adhesive material.

In a preferred embodiment, the venting medium is a complete, unstructured venting layer that covers the plurality of access openings and the related surface.

In the following, the sensor support assembly is separated into individual sensor devices or groups of sensor devices, e.g. by sawing or laser cutting.

In a preferred embodiment, the venting medium is not pre-structured and especially not pre-patterned to match the eventual patterning of the surface of the sensor support assembly. Hence, any alignment process becomes redundant in the attachment of the venting medium.

In a preferred embodiment, prior to separating the sensor support assembly into sensor devices, top elements are deposited on parts of the venting medium. The top elements may contain alignment and/or separation marks which aid the separation also referred to as singulation. The top elements may also ease sensor device singulation and protect the venting medium during and after singulation. Additionally, the top elements may be processed with labels, e.g. detailing the device type or the individual device, either before or after the singulation process.

In a preferred embodiment, the venting medium is fixed on a transfer support. In a preferred embodiment, the transfer support is based on or made of polyester. In one embodiment, the transfer support is removed after attachment of the venting medium to the sensor support assembly, before or after separating the sensor support assembly into individual sensor devices or groups of sensor devices. In another embodiment, a gas permeable transfer support, e.g. mesh or scrim, may remain on the structure.

The described embodiments similarly pertain to the sensor and the method. Synergetic effects may arise from different combinations of the embodiments although they might not be described in detail.

While it is preferred that the order of method steps is as listed in the claims, a different order shall be encompassed by the subject method claims, too, where technically applicable.

Other advantageous embodiments are listed in the dependent claims as well as in the description below.

BRIEF DESCRIPTION OF THE DRAWINGS

Embodiments of the present invention, aspects and advantages will become apparent from the following detailed description thereof. Such description makes reference to the annexed drawings, wherein the figures show.

DETAILED DESCRIPTION

Figure 1:
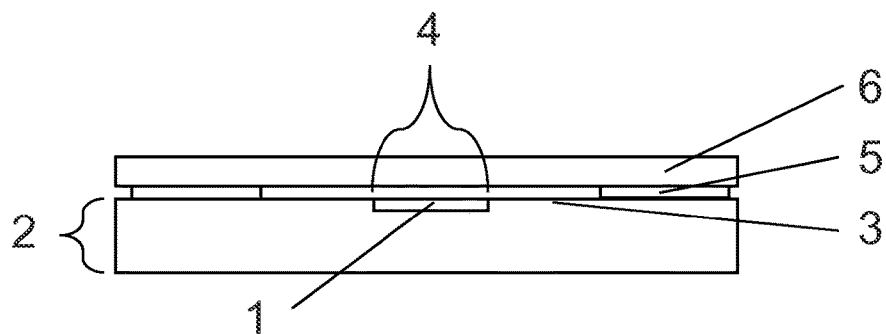
FIG. 1a) to d) schematic sectional views of sensor devices in accordance with examples of the invention.
Figure 1:
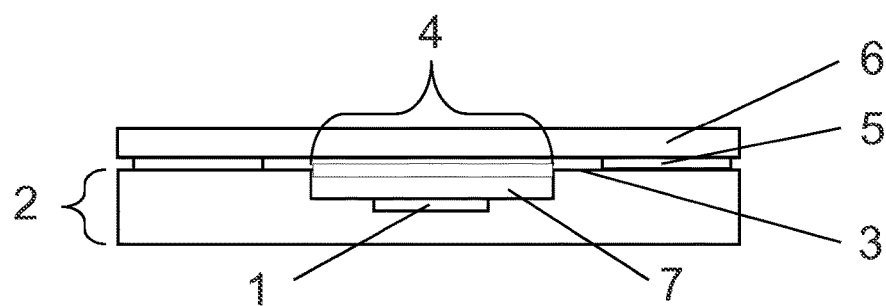
Figure 1:
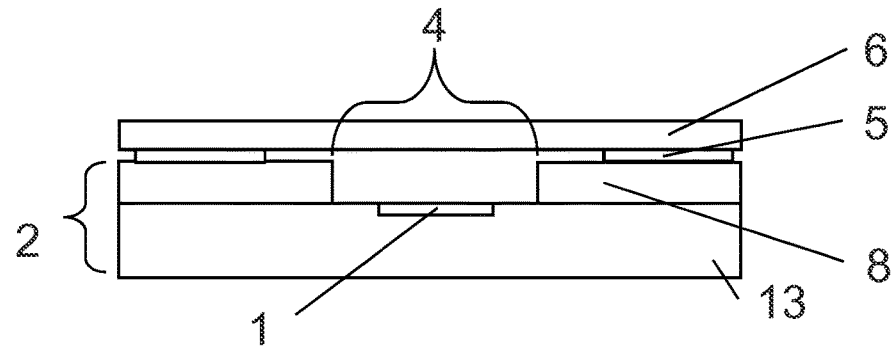
Figure 1:
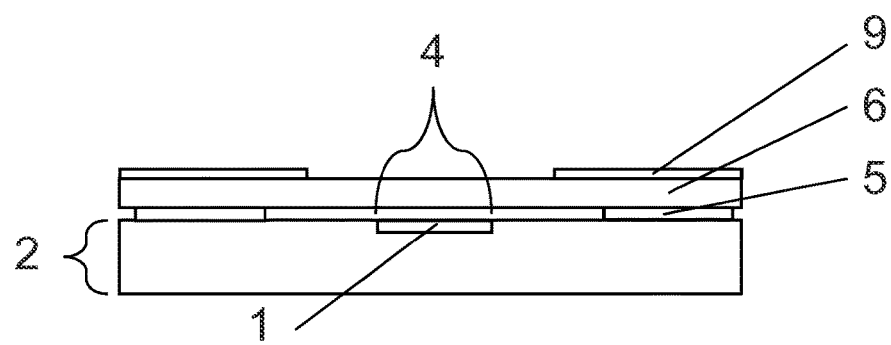

FIG. 1a) shows a schematic sectional view of a sensor device in accordance with an embodiment of the present invention. The sensor device includes a sensitive element 1, which is integrated in a support 2. In this embodiment, the support 2 is a semiconductor substrate, e.g. a silicon substrate, and it may include additional features, such as a heater structure, a suspended membrane, an integrated processing circuit, through silicon vias and solder balls. The gas to be sensed can enter the sensitive element 1 via the access opening 4 which is located in a surface 3 of the support 2. Parts of the surface 3 are covered by a layer of adhesive material 5. A venting medium 6 extends over the entire surface 3 of the support 2 and the access opening 4 and is attached to the support 2 by the layer of adhesive material 5.

FIG. 1b) shows another embodiment of a sensor device in accordance with the present invention. In this embodiment, the sensitive element 1 is located in a cavity 7 in the support 2. The cavity 7 opens out into the surface 3 and thereby defines the access opening 4.

FIG. 1c) illustrates another embodiment of a sensor device in accordance with the present invention. In this embodiment, the support 2 of the sensor device contains a spacer material 8 on top of a silicon substrate 13, for example.

FIG. 1d) shows another embodiment of a sensor device in accordance with the present invention. In this embodiment, the sensor device comprises a top element 9 on a part of the venting medium 6. The top element 9 may serve as protection for the venting medium. Also, it may contain labels and/or alignment marks. The top element 9 may be made from silicon, glass, polymer or any other material that serves one or several of the aforementioned purposes.

Figure 2:
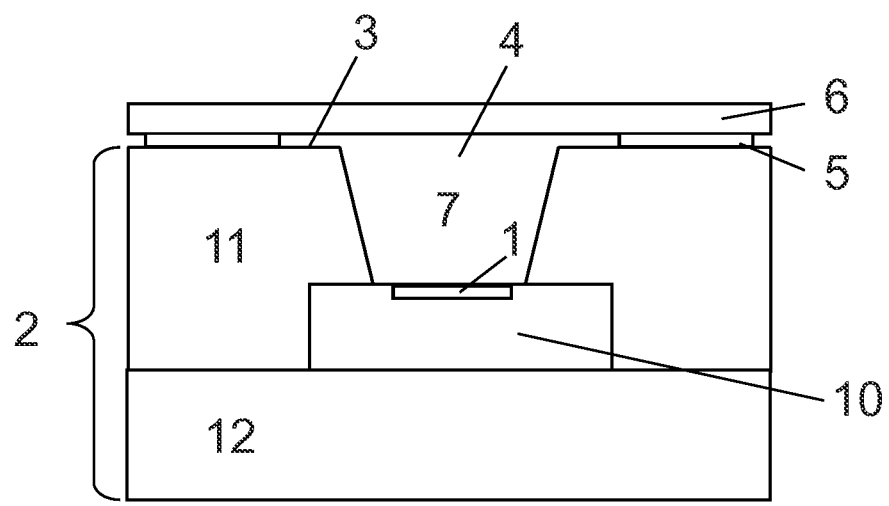
FIG. 2a) to c) schematic sectional views of sensor devices in accordance with examples of the invention.
Figure 2:
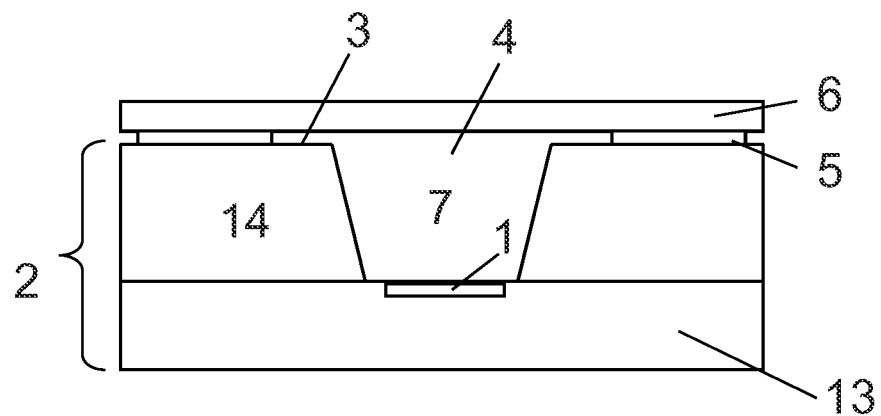
Figure 2:
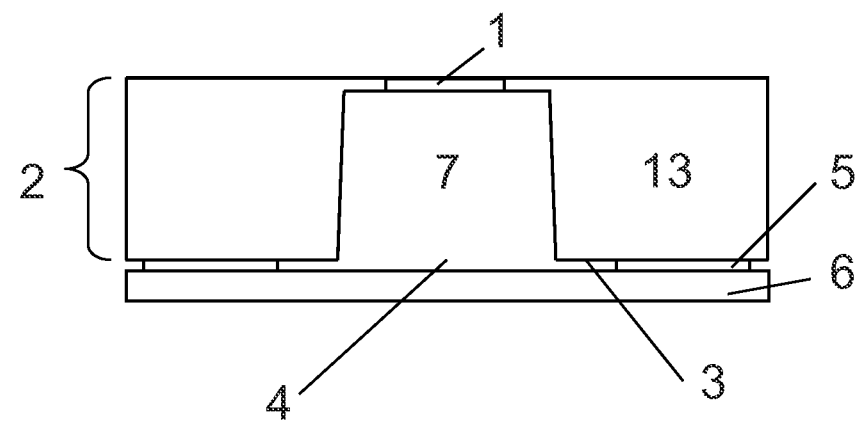

FIG. 2a) illustrates another embodiment of a sensor device in accordance with the present invention. In this embodiment, the sensor device comprises a die 10 with the sensing element 1. The die 10 may include additional features, such as a heater structure, a suspended membrane, an integrated processing circuit. The die 10 is partly covered by a mold 11 and a lead frame 12 serves for outside contacting. A cavity 7 is formed by the die 10 and the mold 11. The cavity 7 opens out into the surface 3 and thereby defines the access opening 4. A venting medium 6 extends over the entire surface 3 of the support 2 and the access opening 4 and is attached to the support 2 by the layer of adhesive material 5.

FIG. 2*b*) illustrates another embodiment of a sensor device in accordance with the present invention. In this embodiment, the sensor device comprises a silicon substrate 13 with the sensitive element 1. The silicon substrate 13 may include additional features, such as a heater structure, a suspended membrane, an integrated processing circuit, through silicon vias and solder balls. The silicon substrate 13 is partly covered by a silicon cap 14. A cavity 7 is formed by the silicon substrate 13 and the silicon cap 14. The cavity 7 opens out into the surface 3 and thereby defines the access opening 4. A venting medium 6 extends over the entire surface 3 of the support 2 and the access opening 4 and is attached to the support 2 by the layer of adhesive material 5.

FIG. 2*c*) illustrates another embodiment of the sensor device in accordance with the present invention. The support 2 contains a substrate, and in particular a silicon substrate 13. A sensitive element 1 is arranged on a suspended membrane portion of the silicon substrate 13 which suspended membrane, for example, is prepared by etching substrate material from a backside of the silicon substrate 13. Hence, a cavity 7 is generated which opens out to the backside of the silicon substrate 13. As a result, the support 2 provides an access opening 4 at its backside. For this reason, the relevant surface 3 of the support 2 is at its backside such that the venting medium 6 is attached to the surface 3 at the backside of the support 2 by means of the layer of adhesive material 5.

Figure 3:
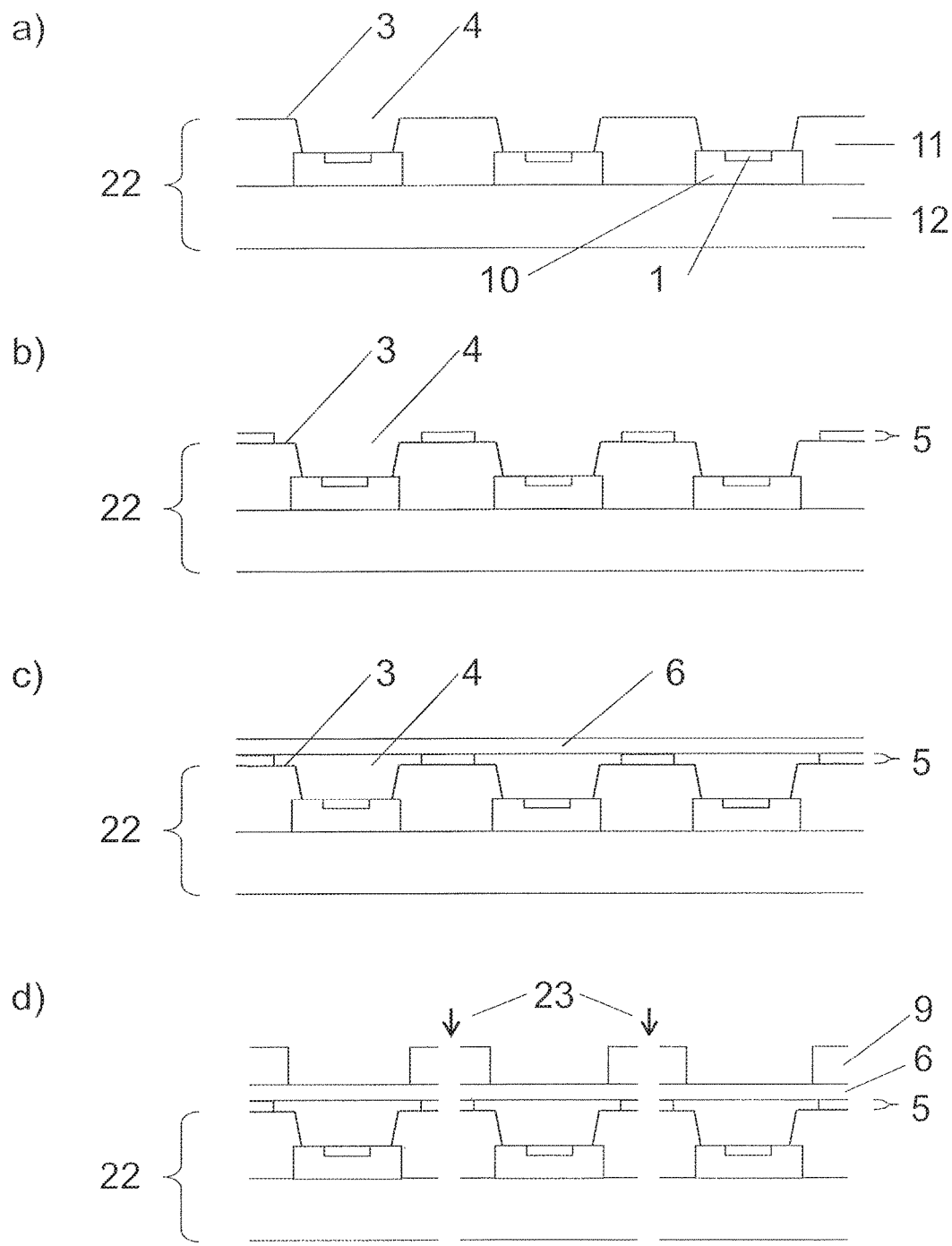
FIG. 3 in its diagrams a) to d) steps of manufacturing a sensor device in accordance with an example of the invention.

FIG. 3 illustrates in its diagrams a) to d) steps of manufacturing a sensor device in accordance with an example of the invention.

In FIG. 3*a*) a sensor support assembly 22 containing an array of sensitive elements 1 for manufacturing a plurality of sensor devices is provided. In this embodiment, the sensor support assembly 22 comprises a plurality of dies 10 which are partly covered by a mold 11. The dies 10 may include additional features, such as a heater structure, a suspended membrane, an integrated processing circuit. A lead frame 12 serves for outside contacting. The sensor support assembly 22 has a surface 3 with access openings 4 to the sensitive elements 1.

In FIG. 3*b*) a layer of adhesive material 5 is applied to parts of the surface 3 of the sensor support assembly 22 which surface 3 contains the access openings 4.

In FIG. 3*c*) a venting medium 6 is arranged over the entire surface 3 of the sensor support assembly 22 and the access openings 4. The venting medium 6 is attached to the sensor support assembly 22 by the layer of adhesive material 5. In this embodiment, the venting medium is not pre-structured and especially not pre-patterned to match the patterning of the surface of the sensor support assembly. The venting medium is a complete, unstructured venting layer that covers the plurality of access openings and the related surface.

For this step it may be helpful that the venting medium is attached during the transfer to a transfer substrate. This may facilitate the handling of the venting medium and protect it against damage. Here, in this embodiment, the transfer layer is removed after the transfer.

In FIG. 3*d*) the sensor support assembly 22 is separated 23 into individual sensor devices or groups of sensor devices. Sensor device singulation may e.g. be implemented by dicing or laser cutting or any other singulation technique. In this embodiment, a top element 9 was placed on the venting medium before sensor device singulation 23. This may serve as protection for the venting medium, especially during the singulation and to ease the singulation process itself. The top element 9 may also contain separation marks and/or alignment marks facilitating the separation process. It may also contain labels and/or identification marks which may provide information on the sensor device, e.g. a device number, or sensor device type, e.g. a product number or type.

Figure 4:
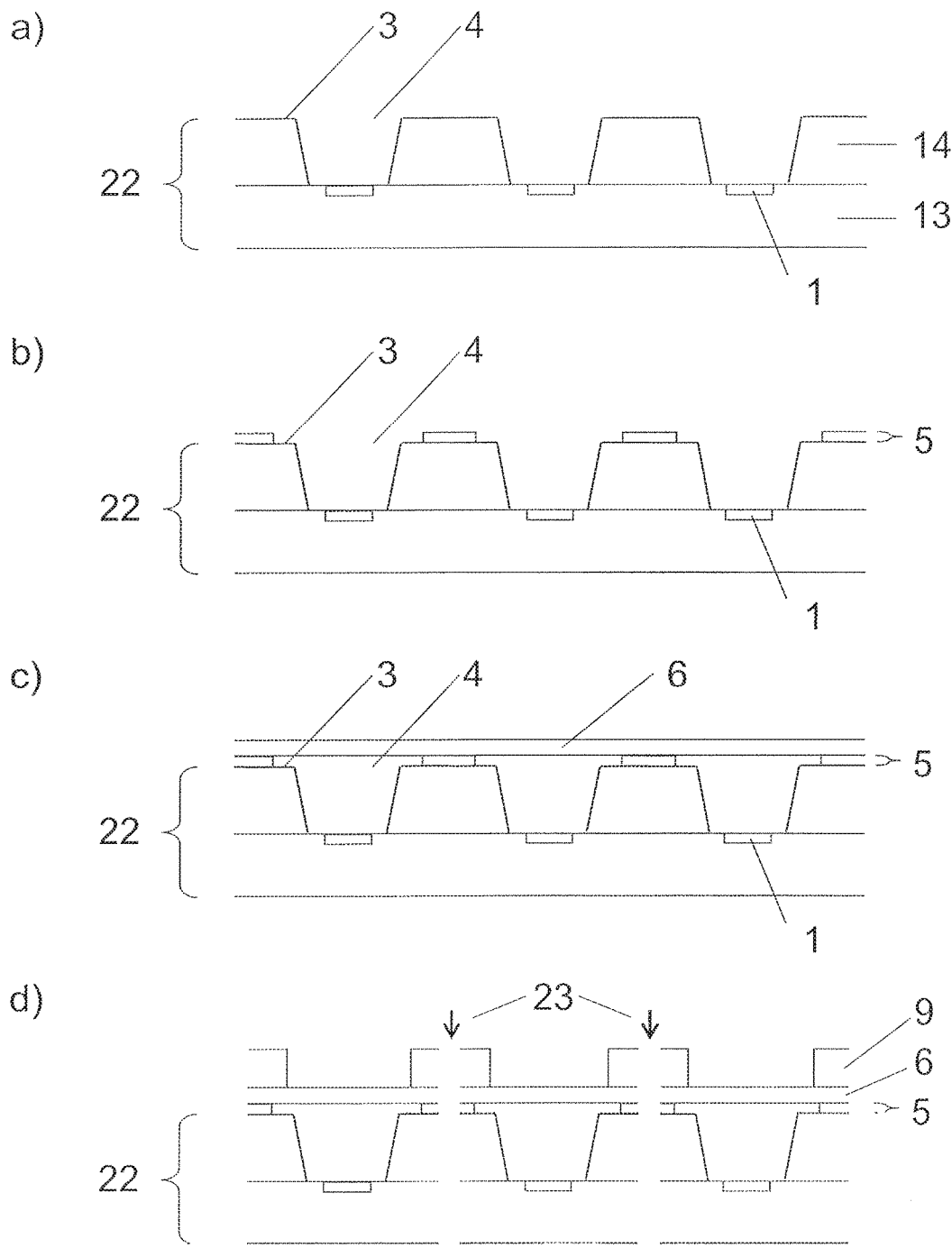
FIG. 4 in its diagrams a) to d) steps of manufacturing a sensor device in accordance with another example of the invention.

FIG. 4 illustrates in its diagrams a) to d) steps of manufacturing a sensor device in accordance with another example of the invention.

In FIG. 4*a*) a sensor support assembly 22 containing an array of sensitive elements 1 for manufacturing a plurality of sensor devices is provided. In this embodiment, the sensor support assembly 22 comprises a semiconductor substrate 13 which is partly covered by a silicon cap 14. Instead of the silicon cap 14, a mold structure may be provided, too. The sensor support assembly 22 has a surface 3 with access openings 4 to the sensitive elements 1.

In FIG. 4*b*) a layer of adhesive material 5 is applied to parts of the surface 3 of the sensor support assembly 22 which surface 3 contains the access openings 4.

In FIG. 4*c*) a venting medium 6 is arranged over the entire surface 3 of the sensor support assembly 22 and the access openings 4. The venting medium 6 is attached to the sensor support assembly 22 by the layer of adhesive material 5. In this embodiment, the venting medium 6 is not pre-structured and especially not pre-patterned to match the patterning of the surface of the sensor support assembly. The venting medium is a complete, unstructured venting layer that covers the plurality of access openings and the related surface.

For this step it may be helpful that the venting medium is attached during to a transfer substrate. This may facilitate the handling of the venting medium and protect it against damage. The transfer substrate can remain entirely or in parts on the venting medium.

In FIG. 4*d*) the sensor support assembly 22 is separated 23 into individual sensor devices or groups of sensor devices. Sensor device singulation may e.g. be implemented by dicing or laser cutting or any other singulation technique.

In this embodiment a top element 9 was placed on the venting medium before sensor device singulation 23. This may serve as protection for the venting medium, especially during the singulation. The top element 9 may also contain separation marks and/or alignment marks facilitating the separation process. It may also contain labels and/or identification marks which may provide information on the sensor device, e.g. a device number, or sensor device type, e.g. a product number or type.

It should further be noted that in any removal of material during manufacturing, the corresponding structures may be created using a chemical (wet) etching process, plasma etching process, laser cutting, mechanical milling or a combination of any of these processes, where suitable.

While above there are shown and described embodiments of the invention, it is to be understood that the invention is not limited thereto but may be otherwise variously embodied and practised within the scope of the following claims.

The invention claimed is:
1. A sensor device, comprising:
 a sensitive element,
 a support for the sensitive element, the support having a surface with an access opening to the sensitive element,
 a layer of adhesive material covering at least parts of the surface, and
 a venting medium
  comprising a layer, a multi-layer or a film, enabling gas to pass through the venting medium while liquids and contaminants are in essence repelled, extending over the entire surface of the support and the access opening and being attached to the support by the layer of adhesive material, and a top element protruding from a part of the venting medium, wherein the top element comprises an element for protecting the venting medium, and wherein the top element includes one or more of: polymer, filled polymer, mold compound, silicon, glass, metal, wherein the access opening enables the gas passed through the venting medium to access the sensitive element and wherein the venting medium contains one or more of a polymer, a fluoropolymer, PTFE, an acrylic copolymer, a polyethersulfone polymer, glass fiber, porous organic material and porous inorganic material.

2. The sensor device of claim 1,
wherein the sensitive element is sensitive to one or more of:
pressure
gas
humidity
gas flow
differential pressure.

3. The sensor device of claim 1,
wherein the sensitive element is located in a cavity in the support,
and wherein the cavity opens out into the surface and thereby defines the access opening.

4. The sensor device of claim 1,
wherein the support comprises one or more of a substrate and a carrier, and a spacer material between the layer of adhesive material and the substrate or the carrier respectively.

5. The sensor device of claim 1,
wherein the support contains one or more of:
a die
a mold
a lead frame
a silicon substrate
a silicon cap
a semiconductor substrate
a ceramic substrate
a glass substrate
a printed circuit board
a ball grid array
a land grid array
through-silicon vias
wire-bonds
T-contacts
a silicon interposer
a heater structure
a suspended membrane
an integrated processing circuit.

6. The sensor device of claim 1,
wherein the venting medium extends over the entire surface and the access opening and wherein another venting medium is attached to another surface of the support opposite the surface containing the access opening.

7. A method for manufacturing a sensor device, comprising:
providing a sensor support assembly containing an array of sensitive elements for manufacturing a plurality of sensor devices, the sensor support assembly having a surface with access openings to the sensitive elements, depositing a layer of adhesive material on at least parts of the surface of the sensor support assembly which surface contains the access openings, arranging a venting medium over the entire surface of the sensor support assembly and the access openings, which venting medium comprises a layer, a multi-layer or a film and which venting medium enables the passage of gas through the venting medium while liquids and contaminants are in essence repelled, wherein the venting medium is attached to the sensor support assembly by the layer of adhesive material such that the access opening enables the gas passed through the venting medium to access the sensitive element and wherein the venting medium contains one or more of a polymer, a fluoropolymer, PTFE, an acrylic copolymer, a polyethersulfone polymer, glass fiber, porous organic material and porous inorganic material, depositing one or more top elements on parts of the venting medium prior to separating the sensor support assembly such that the one or more top elements protrude from the parts of the venting medium, wherein the one or more top elements comprise a protection for the venting medium, and wherein the one or more top elements includes one or more of: polymer, filled polymer, mold compound, silicon, glass, metal, and separating the sensor support assembly into individual sensor devices or groups of sensor devices.

8. The method of claim 7,
wherein the venting medium is not pre-structured.

9. The method of claim 7,
wherein the venting medium is fixed on a transfer support, which is entirely or partly removed after attachment of the venting medium to the sensor support assembly, before or after separating the sensor support assembly into individual sensor devices or groups of sensor devices.

10. The method of claim 7,
wherein the sensor support assembly contains one or a more of:
a die
a mold
a lead frame
a silicon substrate
a silicon cap
a semiconductor substrate
a ceramic substrate
a glass substrate
a temporary carrier
a printed circuit board
a ball grid array
a land grid array
wire-bonds
through-silicon vias
T-contacts
a silicon interposer
a heater structure
a suspended membrane
an integrated processing circuit.

11. The method of claim 7,
wherein the layer of adhesive material is deposited on at least parts of the surface of the sensor support assembly by one or more of:
printing
dispensing
stamping spin coating
lamination
a structuring process
photo-lithography.

* * * * *